United States Patent [19]
Mukherjee et al.

[11] Patent Number: 5,810,716
[45] Date of Patent: Sep. 22, 1998

[54] ARTICULATED MANIPULATOR FOR MINIMALLY INVASIVE SURGERY (AMMIS)

[75] Inventors: Ranjan Mukherjee, Lansing, Mich.; Gangbing Song, Pacific Grove, Calif.

[73] Assignee: The United States of America as represented by the Secretary of the Navy, Washington, D.C.

[21] Appl. No.: 756,827

[22] Filed: Nov. 15, 1996

[51] Int. Cl.$^6$ ...................................................... A61B 1/00
[52] U.S. Cl. ........................ 600/146; 600/139; 600/141; 600/142
[58] Field of Search ................................... 600/139, 141, 600/142, 146, 147, 148, 149, 150, 151, 143, 144

[56] References Cited

U.S. PATENT DOCUMENTS

| | | | |
|---|---|---|---|
| 4,726,355 | 2/1988 | Okadq | 600/141 X |
| 5,005,558 | 4/1991 | Aomori | 600/141 |
| 5,086,401 | 2/1992 | Glassman et al. . | |
| 5,174,277 | 12/1992 | Matsumaru | 600/142 |
| 5,330,502 | 7/1994 | Hassler et al. . | |
| 5,346,504 | 9/1994 | Ortiz et al. . | |
| 5,383,888 | 1/1995 | Zvenyatsky et al. . | |
| 5,403,342 | 4/1995 | Tovey et al. . | |
| 5,405,344 | 4/1995 | Williamson . | |
| 5,409,498 | 4/1995 | Braddock et al. . | |
| 5,417,203 | 5/1995 | Tovey et al. . | |
| 5,480,407 | 1/1996 | Shaw et al. . | |
| 5,487,377 | 1/1996 | Smith et al. . | |

OTHER PUBLICATIONS

Mueglitz et al., Problems of Manipulators for Minimal Invasive Surgery, Endoscopic Surgery, pp. 160–164, 1993.
Cohn et al., Surgical Applications of Milli–Robots, Journal of Robotic Systems, pp. 401–416, 1995.

*Primary Examiner*—Beverly M. Flanagan
*Attorney, Agent, or Firm*—Donald E. Lincoln

[57] ABSTRACT

A mechanism is described to provide dexterity through articulation. The mechanism includes a plurality of concatenated segments for transferring angular rotational motion from a driving device located at its base to the distal end. Each segment in the mechanism acts as both a driven element and a driving element whereby each segment is articulated so that the total articulation of the mechanism is the sum of the articulation motions of each segment.

4 Claims, 5 Drawing Sheets

ARTICULATED MANIPULATOR FOR MINIMALLY INVASIVE SURGERY (AMMIS)

BACKGROUND OF THE INVENTION

This invention relates to medical devices used in minimally invasive surgery and more particularly to an improved dexterous tool for minimally invasive surgical procedures. The surgical manipulator will also be ideally suited for tele-surgery.

SUMMARY OF THE INVENTION

Minimally invasive surgery has been widely accepted as a safe and cost-effective procedure as millions of such procedures have been performed to date. A current limitation in minimally invasive surgical procedures, laparoscopic surgery for example, is the lack of an externally controllable articulated robotic manipulator which will be able to freely maneuver within the torso while supporting a surgical tool such as a pair of scissors, or an optical device such as a camera, or both. In the case of laparoscopic surgery, the surgical instrument commonly used is a single-purpose rigid link supporting either a surgical tool or a camera. The existing state-of-the-art in dexterous manipulators involve a rigid link with a short tip that can bend up to 90 degrees uni-directionally. This system provides better maneuvering capability than a completely rigid tool, but is far from providing the desired level of dexterity of manipulation that a surgeon would like to have. A surgeon may need to approach an internal organ within the torso with an arbitrary orientation, such as in the case of inserting a catheter inside the common bile duct for exploration and or removal of stones. Such procedures are quite difficult to perform in the absence of greater manipulator dexterity.

A dexterous minimally invasive surgical manipulator should meet the following requirements:

(a) It should be small enough to pass through a standard trocar sleeve 10 millimeter (mm) or less in diameter,
(b) it should be able to bend up to 180 degrees, bi-directionally,
(c) it should be able to apply sufficient forces as required to perform common minimally invasive surgical procedures, and
(d) it should be able to support a surgical tool or an optical device, or both a surgical tool and an optical device.

DESCRIPTION OF THE INVENTION

The design objective of the articulated manipulator for minimally invasive surgery (AMMIS) is to achieve dexterity with the minimum number of actuators. The use of fewer actuators enables the miniaturization of the articulated structure and provides additional space for the accommodation of peripheral devices that add functionalities to the manipulator.

The central idea behind the manipulator (AMMIS) design is to concatenate a series of linkages in which every link is both a driven-link and a driving-link. Using this idea, the power from a single actuator located at the base link can be transmitted to the end of the chain of linkages while providing articulation to each and every one of the linkages.

Figure 1:
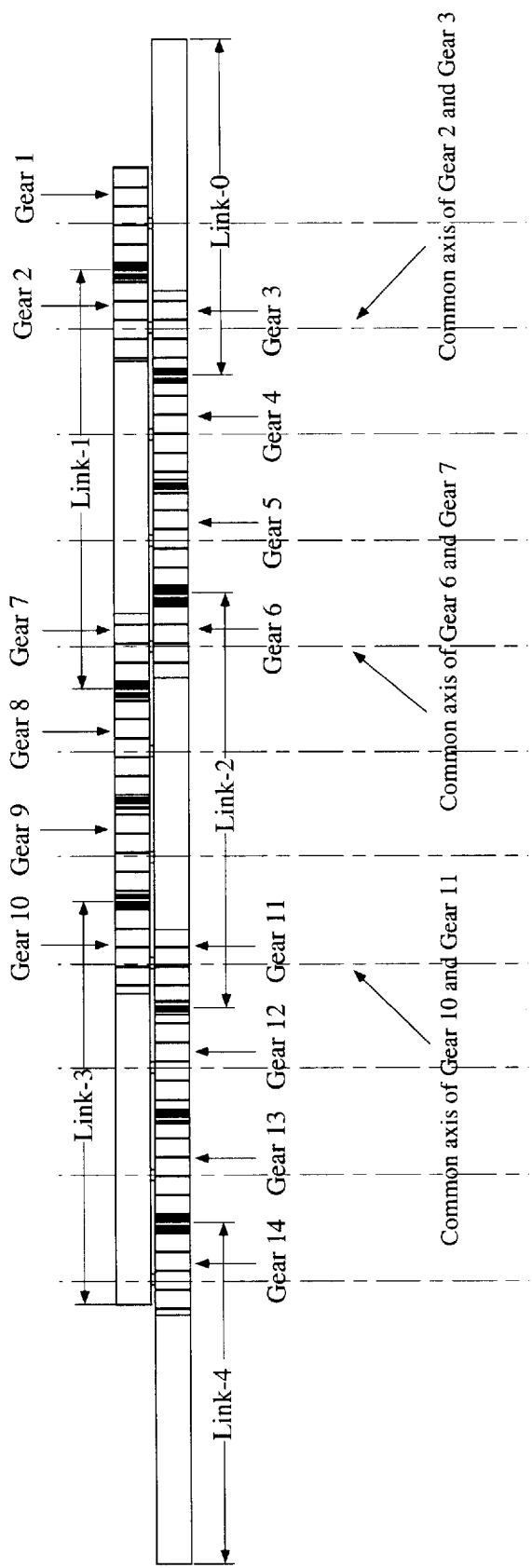
FIG. 1 is a Plan View of a 4-Link AMMIS
Figure 2:
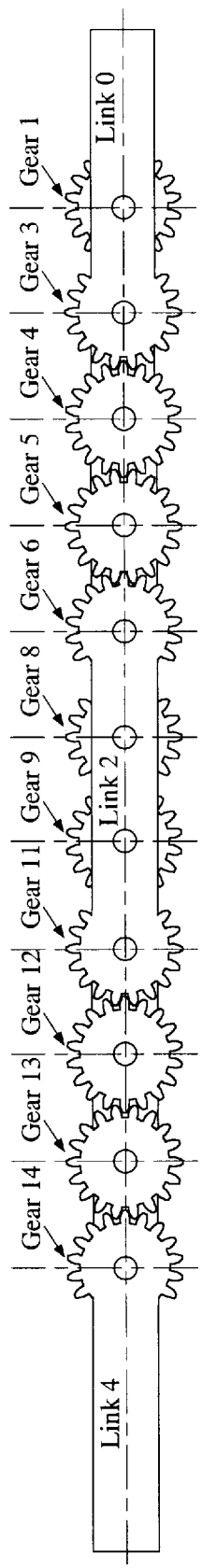
FIG. 2 is a Side View of a 4-Link AMMIS

The conceptual manipulator discussed above can be realized by the mechanism illustrated in FIGS. 1 and 2. FIG. 1 depicts the plan view of a four-link articulated manipulator chain with a single actuator located on Link-0 which serves as the base of the manipulator. FIG. 2 depicts the side view of the mechanism. Gear-1 is the actuator or the driving gear and can be connected to a servo-motor or can be driven manually. All gears in this particular design have the same pitch number and the same pitch diameter—this only simplifies our discussion and is not a limitation of our manipulator design.

We first notice that Gear-2 is rigidly connected to Link-1. As the driving gear, Gear-1, rotates $\beta$ degrees clockwise, Gear-2 and Link-1 will simultaneously rotate $\beta$ degrees in the counter-clockwise direction about the common axes of Gear-2 and Gear-3. Gear-4 is mounted on Link-1 and is meshed with Gear-3 which cannot rotate about its own axis. Therefore, as Link-1 rotates counter-clockwise, Gear-4 behaves as a planetary gear to Gear-3 and rotates counter-clockwise about its own axis. Gear-5 is meshed together with Gear-4 and Gear-6. Thus Gear-6 rotates $\beta$ degrees counter-clockwise as Gear-4 rotates $\beta$ degrees counter-clockwise. Gear-6 is rigidly connected to Link-2; this implies that Link-2 will rotate $\beta$ degrees in the counterclockwise direction with respect to Link-1 about the common axes of Gear-6 and Gear-7 as viewed from the side illustrated in FIG. 2. As Gear-6 rotates $\beta$ degrees counter-clockwise, Gear-8 behaves as a planetary gear to Gear-7 which cannot rotate about its own axis relative to Link-1.

Figure 3:
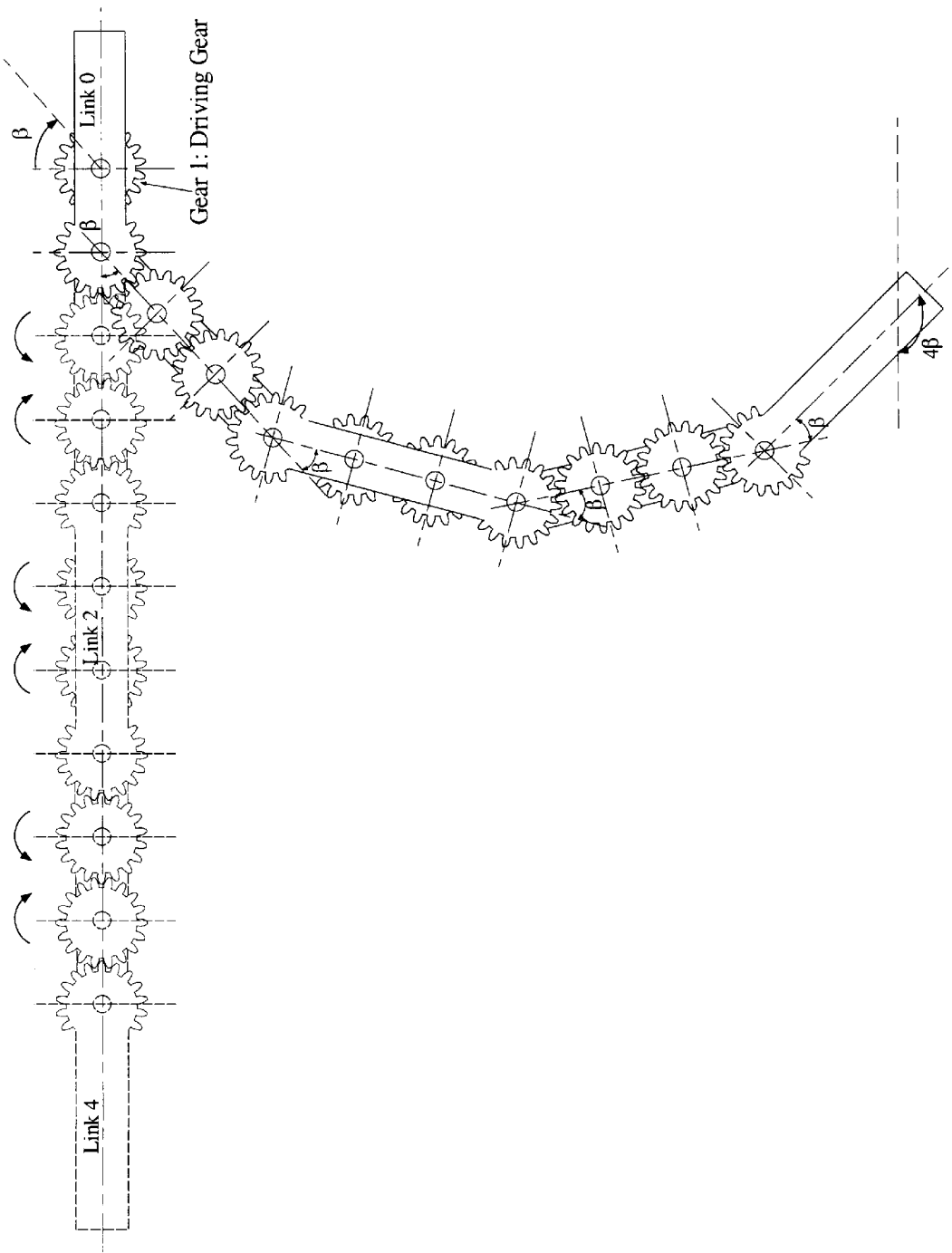
FIG. 3 is a Side View of the AMMIS in an articulated configuration.

Using the same reasoning as above, we can show that Link-3 will rotate $\beta$ degrees counter-clockwise with respect to Link-2 about the common axes of Gear-10 and Gear-11, and Link-4 will also rotate $\beta$ degrees counter-clockwise with respect to Link-3 about the axis of Gear-14. Therefore, we have a mechanism where each link rotates $\beta$ degrees counter-clockwise with respect to the previous link as the driving gear rotates $\beta$ degrees clockwise. In effect, we achieve a total of 4 $\beta$ degrees counterclockwise rotation at the end of Link-4 of this four link AMMIS (articulated manipulator for minimally invasive surgery) with respect to the base link, Link-0, as shown in FIG. 3.

Figure 4:
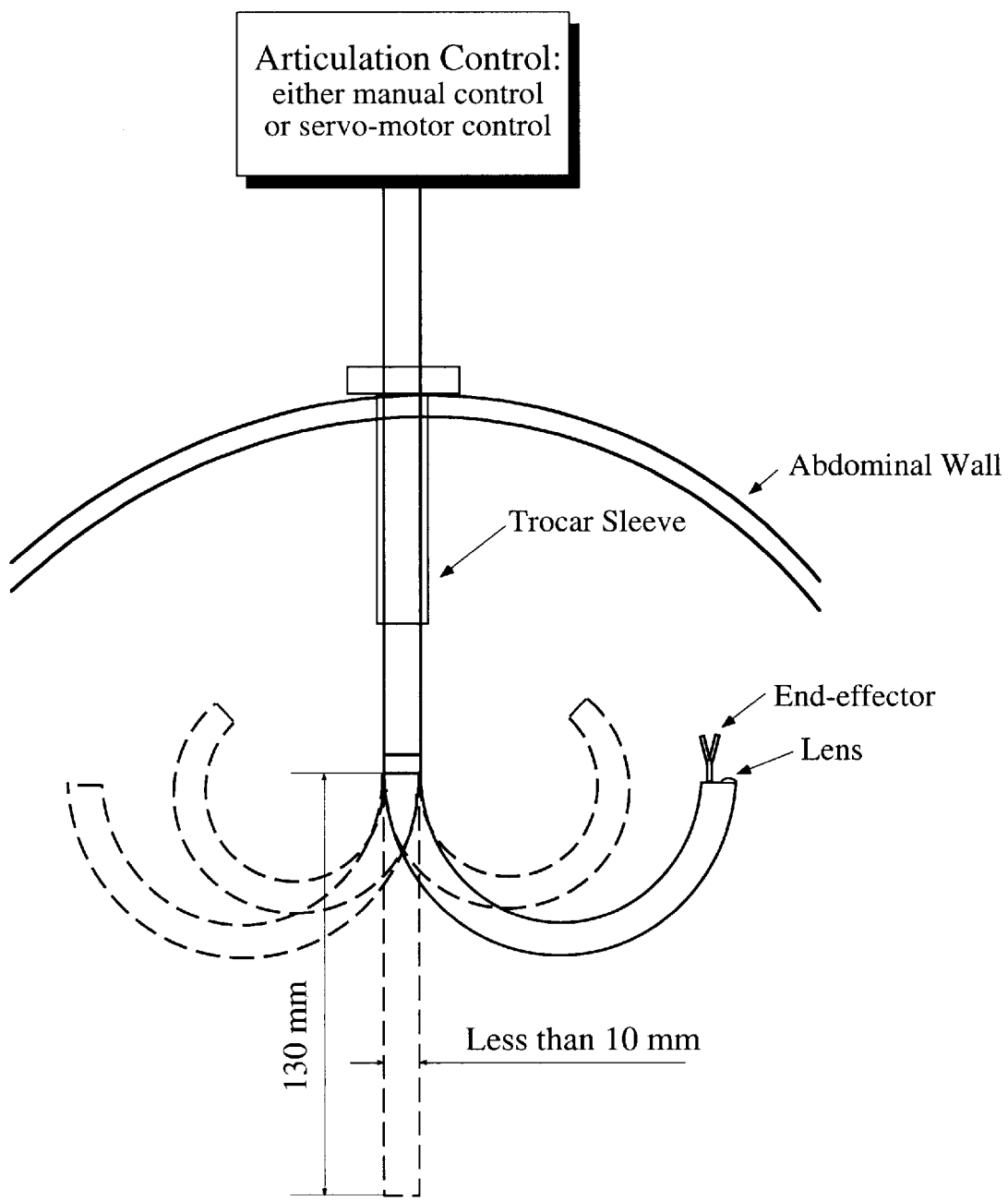
FIG. 4 is a conceptual diagram showing an AMMIS in various configurations during a minimally invasive surgical procedure.
Figure 5:
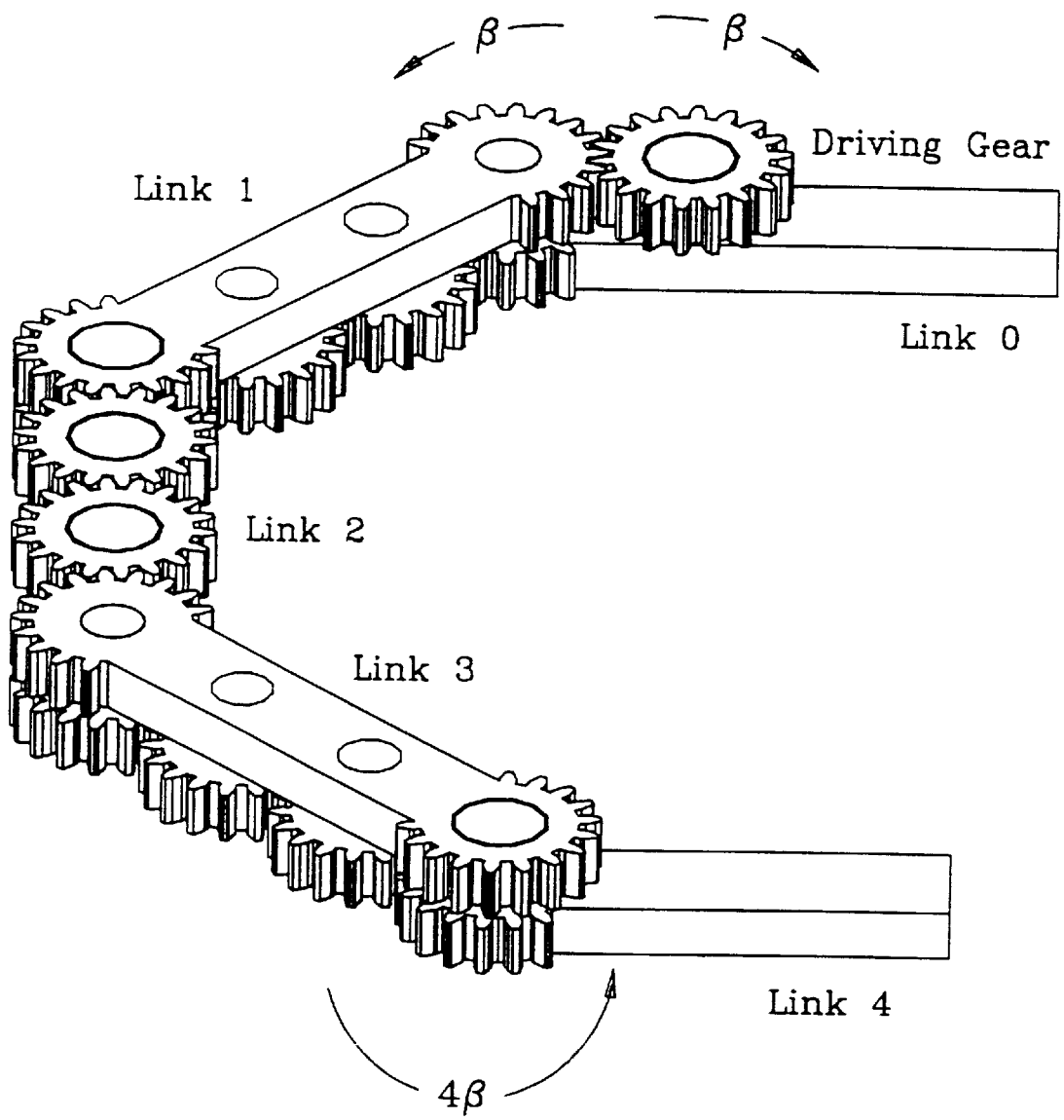
FIG. 5 is a perspective view of a 4-Link AMMIS.

If a larger bend is required, one or more linkages can be added to the 4-link AMMIS to achieve more rotation at the end of the chain. Also, by rotating the driving gear clockwise and counter-clockwise, it is possible to achieve bi-directional articulation of the AMMIS. FIG. 3 shows the AMMIS in solid lines from the side when Gear-1 is rotated clockwise by an angle $\beta$ and in broken lines when the links of the AMMIS are aligned with each other. A schematic of the AMMIS in various configurations during a minimally invasive surgical procedure is shown in FIG. 4. The dimensions shown in this embodiment are by way of example only.

The articulated manipulator for minimally invasive surgery (AMMIS) has the following advantages and new features:

(a) The compact and simple mechanical design of the AMMIS makes miniaturization possible such that it can pass through a, for example, 10 mm (0.39 inch) or smaller standard trocar sleeve during a minimally invasive surgical procedure. The mechanical design of the AMMIS is scaleable for further minimization so that it can pass through a trocar sleeve 5 mm in size while carrying a single end-effector.

(b) The AMMIS is capable of carrying a miniature camera, for example, 5 mm (0.20 inch) in diameter commercially available at present, along with an end-effector such as a pair of scissors or a gripper. Unlike the single-purpose instruments that are currently in use, the manipulator will prove to be a multi-purpose surgical tool.

(c) The AMMIS is capable of dexterous manipulation. It can be designed to follow a serpentine path of tight radii and make bends of 180 degrees or more bi-directionally, by using even and odd number of gears in successive links, or by using a plurality of actuators.

(d) The AMMIS has sufficient structural rigidity to generate forces that would be required during surgical procedures, such as cutting, sowing, etc.

(e) The AMMIS is close to a perfectly linear system since the angular motion of each link is proportional to the rotation of the actuator. Its simple and compact design simplifies the control of its articulated motion. The AMMIS provides quick response time to transmit motion from the actuator to the various links of the AMMIS.

(f) The compact nature of the design, the simplicity of control and the quick response time of the AMMIS makes it an ideal candidate for tele-surgery.

Currently, there are a number of articulated manipulators in the research stage. These are usually driven by Shape Memory Alloy (SMA) actuators or tendons. Our manipulator is superior to these articulated manipulators as it offers all the desired characteristics of a surgical manipulator, as mentioned above. Shape Memory Alloy wire actuated manipulators cannot make sharp bends though it can apply large forces. Manipulators employing Shape Memory Alloy springs can make sharp bends but cannot apply large forces. Moreover, Shape Memory Alloy actuators have a slow response. Articulated manipulators using tendon drives are inherently difficult to control. Moreover, tendon driven manipulators cannot be easily miniaturized.

Instead of using gears as the driving mechanism other mechanisms such as friction wheels, pulleys and tendons, sprockets and chains, wheels and connecting rods, etc. can be employed to achieve similar articulated motion of the surgical manipulator.

In the AMMIS design presented here, the magnitude of rotation between adjacent linkages were the same and were equal to the magnitude of rotation of the driving gear. This is due to the fact that the gear ratios between adjacent linkages were chosen to be unity. The magnitudes of rotation of adjacent linkages can be made to differ by choosing gears of varying pitch diameter. This can be used for achieving different shapes of articulation.

In the AMMIS design presented here, each linkage has two gears for the transmission of power from the previous link to the next. An addition of an even number of gears to any particular linkage will enable us to change the length of that link and hence the shape of articulation of the manipulator, while maintaining the uniformity in the direction of rotation of every linkage. If an odd number of gears are added to a link, the direction of rotation of the next link is reversed with respect to that particular link. In other words, an AMMIS can be designed to achieve various forms of articulation using different number of gears per link while using only a single driving mechanism.

Though the embodiment of the AMMIS, discussed above, can provide a substantial degree of articulation, it is essentially a single degree-of-freedom mechanism since the different links of the AMMIS cannot be moved independently relative to each other. An AMMIS can be designed with multiple driving mechanisms (actuators) controlling two connected, yet independently controllable portions of the AMMIS, thereby to achieve multiple degrees-of-freedom for more complex articulation. For example, a plurality of intermeshing gears could be provided on a first portion, extending from the proximal end of the first portion to its distal end, thereby to manipulate a second portion connected to the distal end of the first portion. In such an embodiment, the first and second portions together constitute a complex two-actuator AMMIS with two independent actuators.

Various modifications, changes and embodiments are shown and described herein; others will be obvious to those skilled in this art. Accordingly, it is intended that the foregoing be illustrative only and not limiting of the scope of the invention.

What we claim is:

1. An articulated device, which comprises:
   a base end;
   a driving device mounted on said base end for imparting articulation motion;
   a distal end; and
   a plurality of concatenated segments interconnecting said base end and said distal end whereby each segment acts as a driven segment and a driving segment for receiving and transferring articulation motion from said driving device to said distal end wherein each segment is articulated and adds further articulation so that the total articulation motion is the sum of the articulation motions of each segment.

2. The articulated device of claim 1, wherein the driving device is a rotational driving device.

3. An articulated device, which comprises:
   a base end;
   said base end having a driving device mounted thereon for imparting a bi-directional angular rotational movement;
   a distal end of said device located at the end opposite said base end for receiving said angular rotational movement; and
   a series of mechanisms interconnected between said base end and said distal end for transferring said angular rotational motions therebetween, wherein each of said mechanisms acts as a driven mechanism and a driver mechanism for transferring said angular movement so that the total articulation motion is the sum of the articulation motion of each mechanism whereby said distal end may be angularly rotated bi-directionally from 0 degrees to more than 180 degrees to provide increased dexterity and agility to said device.

4. An articulated device, which comprises:
   a base end;
   said base end having a rotational driving device mounted thereon for imparting a bi-directional angular rotational movement;
   a distal end of said device located at the end opposite said base end for receiving said angular rotational movement; and
   a series of rotational devices interconnected between said base end and said distal end for transferring said angular rotational motions therebetween using said rotational devices, wherein each of said rotational devices acts as a driven device and a driver device for transferring said angular movement so that the total articulation motion is the sum of the articulation motion of each of said rotational devices whereby said distal end may be angularly rotated bi-directionally from 0 degrees to more than 180 degrees to provide increased dexterity and agility to said articulated device.

* * * * *